United States Patent [19]

Röhrscheid et al.

[11] Patent Number: 5,637,764
[45] Date of Patent: Jun. 10, 1997

[54] PROCESS FOR THE PREPARATION OF BROMINATED OR CHLORINATED AROMATIC CARBOXYLIC ACIDS

[75] Inventors: Freimund Röhrscheid, Kelkheim; Georg Grötsch, Bad Soden, both of Germany

[73] Assignee: Hoechst Aktiengesellschaft, Germany

[21] Appl. No.: 561,922

[22] Filed: Nov. 22, 1995

[30] Foreign Application Priority Data

Nov. 24, 1994 [DE] Germany ............. 44 41 881.7

[51] Int. Cl.⁶ .................................. C07C 51/16
[52] U.S. Cl. ..................................... 562/416
[58] Field of Search ........................... 562/416

[56] References Cited

U.S. PATENT DOCUMENTS

| | | | |
|---|---|---|---|
| 3,681,446 | 8/1972 | Ledford | 260/524 |
| 4,603,220 | 7/1986 | Feld | 562/414 |
| 4,605,757 | 8/1986 | Feld | 562/416 |
| 4,990,659 | 2/1991 | Jihad | 562/416 |
| 5,068,407 | 11/1991 | Periana | 562/416 |

FOREIGN PATENT DOCUMENTS

| | | |
|---|---|---|
| 121684 | 10/1984 | European Pat. Off. |
| 1468858 | 3/1969 | Germany . |
| 3440650 | 3/1986 | Germany . |

OTHER PUBLICATIONS

Abstract of U.S. Pat. No. 4,605,757 (1986).

*Primary Examiner*—Michael L. Shippen
*Attorney, Agent, or Firm*—Connolly & Hutz

[57] ABSTRACT

Process for the preparation of brominated or chlorinated aromatic carboxylic acids The invention relates to a process for the preparation of bromine- or chlorine-substituted aromatic carboxylic acids by oxidation of the correspondingly halogenated alkylaromatics with oxygen or an oxygen-containing gas in the solvent acetic acid and in the presence of a transition metal bromide catalyst, which comprises a procedure in which a) the reaction mixture comprises a sodium and/or potassium salt of a weak acid, b) when the reaction has ended, the reaction solution is cooled and the product which has crystallized is filtered off from the reaction solution, c) the combined mother and wash liquors are dehydrated to a water content of $\leq 1.0\%$ by distillation, d) the alkali metal halide which has precipitated is filtered off from the mother liquor and e) the mother liquor is reused as the reaction medium.

17 Claims, No Drawings

PROCESS FOR THE PREPARATION OF BROMINATED OR CHLORINATED AROMATIC CARBOXYLIC ACIDS

The invention relates to a process for the preparation of brominated or chlorinated aromatic carboxylic acids by oxidation of the corresponding alkylaromatics.

It is known that alkylaromatics can be oxidized with atmospheric oxygen in acetic acid at temperatures above 120° C. to give the corresponding benzoic acids or oligocarboxylic acids in a high yield if the reaction is catalyzed by bromides of the sub-group elements cobalt and manganese (U.S. Pat. No. 2,833,816) or combinations thereof with nickel (U.S. Pat. No. 3,334,135), iron (U.S. Pat. No. DE 2,749,638) or zirconium (U.S. Pat. No. DE 2,420,960).

The oxidation of solutions of alkylbenzenes in acetic acid with atmospheric oxygen to give the corresponding benzoic acids or aromatic oligocarboxylic acids can be carried out in a particularly favorable economic and ecological manner if the mother liquor of the preceding batch can be used again as the reaction medium, since this mother liquor contains the catalyst, some of the product and precursors of the target product (complete yield only when the mother liquor is recycled).

Under the abovementioned conditions, oxidation of halogenated alkylaromatics gives the corresponding carboxylic acids in a high yield (EP 002 749). In the case of oxidation of brominated or chlorinated alkylaromatics, such as, for example, chlorotoluene, dichlorotoluene, bromochlorotoluene, 2-chloro-1,4-dimethylbenzene or 2,4-dimethyl-2'-chlorobenzophenone, however, there is the problem that a small percentage (about 1–3%) of the halogen is split off from the aromatic and is present in the solution as halide or hydrogen halide.

This leads to corrosion problems. To prevent corrosion of the reactor, the addition of alkali metal acetates in an aqueous dilute acetic acid is described as a measure in EP 121 684. Although these conditions reduce corrosion of the reactor, the alkali metal halides formed, NaCl, NaBr, KCl and KBr, have a considerable solubility in aqueous acetic acid, even at a low water content, for example 1–5%. This results in marked enrichment of alkali metal halide in the mother liquor which has been recycled several times. However, high alkali metal halide concentrations again have a corrosive action on high-grade steels, and furthermore lead to the increased formation of troublesome benzyl halide in the product solution. This is of great disadvantage for industrial use of the oxidation reaction, because the benzyl halides are incorporated into the product and their enrichment allows only a reduced number of recyclings of the mother liquor. Furthermore, benzyl halides have a considerable smell and stimulate the production of tears.

EP 121 684 does not indicate a way in which the accumulating alkali metal halide can be sluiced out of the circulation. Rather, a water content of >1% by weight, which promotes the enrichment, is explicitly described in the patent specification in order to achieve the highest possible yield.

There was thus a great need for a process which avoids these disadvantages and allows the chlorinated and brominated aromatic carboxylic acids to be prepared in a high yield without contamination by the corresponding aryl methyl halides.

This object is achieved by a process for the preparation of bromine- or chlorine-substituted aromatic carboxylic acids by oxidation of the correspondingly halogenated alkylaromatics with oxygen or an oxygen-containing gas in the solvent acetic acid and in the presence of a transition metal bromide catalyst, which comprises a procedure in which a) the reaction mixture comprises a sodium and/or potassium salt of a weak acid, b) when the reaction has ended, the reaction solution is cooled and the product which has crystallized is filtered off from the reaction solution, c) the combined mother and wash liquors are dehydrated to a water content of $\leq 1.0\%$ by distillation, d) the alkali metal halide which has precipitated is filtered off from the mother liquor and e) the mother liquor is reused as the reaction medium.

In this procedure, the carboxylic acid formed in a very good yield of usually 90–99% (recycling of the mother liquor) and the alkali metal halide can be isolated separately and without great expenditure. The procedure utilizes the observation that the solubility of the salts NaCl, KCl, NaBr and KBr in the mother liquor becomes very low at a water content below 3% by weight, in particular below 1.0% by weight. It has furthermore been found, surprisingly, that KBr is significantly less soluble than NaBr in a mother liquor with less than 1.0% of water; and NaCl is significantly less soluble than NaBr. Using the procedure described below, it is possible to remove troublesome halide ions, to achieve a constantly low concentration of this alkali metal halide in the mother liquor and to precipitate chloride ions selectively, in addition to bromide ions. The content of bromide ions required as the catalyst is accordingly largely retained.

The following procedure has proved suitable in many cases:

a) the oxidation of the halogen-substituted alkylaromatic is carried out in the presence of the sodium or potassium salt of a weak acid, such as, for example, sodium acetate or potassium acetate. The molar amount of this alkali metal salt is advantageously selected to be greater than the molar amount of halide, which is composed of the cocatalyst bromide and the amount of halide split off during the oxidation from the halogen-substituted alkylaromatic employed. The sodium or potassium salts of the weak acids can be added as salts of aliphatic or aromatic carboxylic acids. Aliphatic acids which can be used are, for example, acetic acid, propionic acid and butyric acid, and aromatic carboxylic acids which can be used are benzoic acid or substituted benzoic acids. It is also possible to add sodium carbonate or hydroxide or potassium carbonate or hydroxide, from which sodium acetate or potassium acetate is formed with the acetic acid present.

b) When the reaction has ended, the reaction solution is cooled to 10° to 60° C., in particular 20° to 30° C. The product which has thereby crystallized out is filtered off and washed with acetic acid.

c) The water formed during the reaction is distilled off from the combined filtrates in a distillation column, until a water content of less than 3%, in particular less than 1%, is established in the mother liquor.

d) The alkali metal halides which are precipitated are filtered off from the mother liquor.

e) Any catalyst losses which have occurred in the mother liquor are supplemented. The mother liquor is recycled into the oxidation reactor and reused as the reaction medium for oxidation of the halogenated alkylaromatic. The amount of alkali metal salt of the weak acid required for an oxidation batch can be added to the reaction solution before the oxidation, step (e), or also already to the mother liquor before the filtration (d) or at the start of the distillation (c). To remove chloride ions, such as are formed, for example, in the oxidation of chloroaromatics, the sodium salt of a weak acid, for example sodium acetate, is preferably added because NaCl then precipitates, but the bromide catalyst constituent mostly remains in solution. To precipitate bromide ions, such as are formed in the oxidation of bromoaromatics, the potassium salt of a weak acid, for example potassium acetate, is preferably used because potassium bromide, in contrast to sodium bromide, has a very low solubility in the acetic acid mother liquor of low water content.

Compounds which contain one or more of the metals cobalt, manganese, zirconium or nickel are very successfully employed as the transition metal bromide catalyst. Catalysts which contain cobalt have proven suitable in many cases.

The process is generally suitable for the preparation of chlorinated or brominated aromatic carboxylic acids. Aromatics are to be understood as meaning all aromatic compounds which are stable under the reaction conditions, for example phenyl or naphthyl. In addition to chlorine and/or bromine, the aromatics can also in addition carry one or more identical or different substituents, such as, for example, fluorine, aryl, nitro, alkoxy, aryloxy, tert-alkyl, $SO_2$-alkyl, $SO_2$-phenyl, keto, phosphonic acid, phosphonoxide, $SO_2$-$NH_2$, triorganylsilyl or perfluorinated alkyl groups.

An important process is that for the preparation of compounds of the formula (I)

$$(R^1-X)_o \underset{(R^2)_p}{\overset{(COOH)_n}{\underset{(Hal)_m}{\bigodot}}} \quad (I)$$

in which:

X is a single bond, oxygen, C=O, $SO_2$, $C(CF_3)_2$, $C(CH_3)_2$, PO-$(C_1-C_6)$-alkyl, PO-phenyl, Si-$(C_1-C_6$-alkyl$)_2$, Si-$(C_1-C_6$-alkyl)-phenyl, Si-(phenyl)$_2$ or —$N_2$—, $R^1$ is substituted or unsubstituted phenyl or naphthyl, Hal is chlorine or bromine, $R^2$ is hydrogen, O-$(C_1-C_6)$-alkyl, tert-alkyl, $SO_2$-$(C_1-C_6)$-alkyl, $SO_2$-$NH_2$, $NO_2$, F, PO-$[(C_1-C_6)$-alkyl$]_2$, PO(OH)-$(C_1-C_6)$-alkyl or PO-(OH)$_2$, n and m are an integer between 1 and 4 and o and p are zero or 1, where n+m+o+p≦6.

A process which is of particular interest is that for the preparation of chlorobenzoic acids, dichlorobenzoic acids, fluorobenzoic acids, bromobenzoic acids, chlorinated and brominated benzophenonecarboxylic acids and chlorinated and brominated biphenylcarboxylic acids.

The following examples are intended to illustrate the process without limiting it thereto.

EXAMPLES

The oxidations are carried out in a 1 l autoclave which can be heated and is equipped with a stirrer, gas inlet tube, reflux condenser and oxygen measurement.

Example 1

Oxidation of 4-chlorotoluene 150.0 g of 4-chlorotoluene, 500 g of glacial acetic acid, 10.0 g of cobalt acetate tetrahydrate, 1.54 g of sodium bromide and 2.46 g of sodium acetate are introduced into the autoclave and the mixture is heated to 155° C. under 15 bar of nitrogen. Air is then passed in, the temperature and pressure are regulated at 160° C./166 bar and the stream of air is adjusted such that the residual oxygen content in the waste gas is 1–3% by volume. The highly exothermic reaction has ended after 30 minutes. After a further 20 minutes, nitrogen is passed in, the reactor is cooled and the product solution is removed at 110° C.

The product solution is cooled to 20° C., while stirring. The crystals are separated off on a suction filter, washed with 270 g of glacial acetic acid and dried. Yield: 167.3 g of 4-chlorobenzoic acid (90.2% of theory), melting point 239°–240° C.

The combined filtrates, called the "mother liquor" (744 g), comprise 27.6 g (3.7% by weight) of $H_2O$, 0.48 g of chloride ions, 0.60 g of bromide ions and 0.97 g of sodium ions.

1st Recycling

The mother liquor is concentrated to 510 g on a distillation column, the water content falling to 0.3% by weight. No precipitate is detectable in the solution. Oxidation: 0.28 g of sodium bromide, 1.15 g of sodium acetate and 150 g of 4-chlorotoluene are added to the concentrated mother liquor. The mixture is reacted and worked up in the manner described above. Yield: 179.3 g (96.6% of theory) of 4-chlorobenzoic acid, melting point 239°–241° C. The mother liquor (737 g) comprises 26.9 g (3.6% by weight) of water, 0.95 g of chloride ions, 0.45 g of bromide ions and 1.92 g of sodium ions.

2nd Recycling

After addition of 1.15 g (0.014 mol) of sodium acetate, the mother liquor is concentrated to 510 g of solution containing 0.4% by weight of water. After cooling to 20° C., 0.46 g of sodium chloride was filtered off. Oxidation: the mixture of the concentrated mother liquor, 150 g of 4-chlorotoluene and 0.30 g of sodium bromide is oxidized as described above. Yield: 197.5 g (96.7% of theory), melting point 238°–240° C. The mother liquor (734 g) comprises 27.2 g (3.7% by weight) of water, 1.17 g of chloride ions, 0.68 g of bromide ions and 2.06 g of sodium ions.

Subsequent Recyclings

After addition of 1.15 g of sodium acetate, the mother liquor is concentrated to 510 g with 0.25% of water. Filtration at 20° C. gives 0.78 g of sodium chloride. The average yield of the subsequent oxidations is 182.5 g (97.9% of theory). The melting point is constant at 238°–240° C. The amount of sodium chloride isolated is maintained at the level of the 3rd recycling in the subsequent mother liquor concentrations: about 0.80 g of NaCl per batch. The amount of chloride dissolved in the mother liquor establishes itself to a range of 1.2±0.2 g. The sodium chloride which has precipitated contains only small amounts of sodium bromide (7 mol %).

Example 2

Oxidation of 2-bromotoluene 256.6 g of 2-bromotoluene, 500 g of glacial acetic acid, 7.5 g of cobalt acetate tetrahydrate, 2.5 g of manganese acetate tetrahydrate, 1.03 g of sodium bromide, 2.46 g of sodium acetate and 2.94 g of potassium acetate are oxidized at 155° C. under 16 bar in the course of 40 minutes in the same manner as in Example 1. The crystals from the product solution, which has been cooled to 20° C., are filtered off with suction, washed three times with 70 g of glacial acetic acid each time and dried. Yield: 178.0 g of 2-bromobenzoic acid (59.0% of theory), melting point 148°–149° C.

The combined filtrates, called the "mother liquor" (761 g), comprise 34.2 g (4.5% by weight) of water, 3.32 g of bromide ions, 0.87 g of sodium ions and 1.17 g of potassium ions.

1st Recycling

The mother liquor is concentrated to 530 g with 0.2% by weight of $H_2O$. 2.02 g of potassium bromide are filtered off from the solution (60° C.). 256.6 g of 2-bromotoluene are mixed with the concentrated mother liquor and 2.94 g (0.03 mol) of potassium acetate and the mixture is oxidized and worked up in the manner described above. Yield: 279.6 g of 2-bromobenzoic acid (92.7% of theory). The mother liquor (810 g) comprises 32.4 g (4.0% by weight) of water, 3.64 g of bromide ions, 0.83 g of sodium ions and 1.68 g of potassium ions.

2nd Recycling

The mother liquor is concentrated to 521 g with 0.3% by weight of water. 3.87 g of KBr are isolated by filtration at 60° C. 256.6 g of 2-bromotoluene are mixed with the concentrated mother liquor and 3.81 g of potassium acetate and the mixture is oxidized and worked up in the manner described above. Yield: 281.2 g of 2-bromobenzoic acid (93.2% of theory). The mother liquor (803 g) comprises 32.9 g (4.1% by weight) of water, 3.46 g of bromide ions, 0.77 g of sodium ions and 1.56 g of potassium ions.

Subsequent Recyclings

The mother liquor is concentrated to 529 g with 0.55% of water. 3.37 g of potassium bromide are filtered off from the solution. The concentrated mother liquor is employed again as the reaction medium for the oxidation in the manner described. In the subsequent oxidations the average yield for 2-bromobenzoic acid is 93.8% of theory. The amount of potassium bromide isolated remains in the order of 3.7 g per batch. 3.1 g (0.0316 mol) of potassium acetate per batch are accordingly added. The amount of bromide ions in the mother liquors is kept below 3.6 g in this manner. The potassium bromide which has precipitated contains only small amounts of sodium bromide.

Example 3

Oxidation of 2,3-dichlorotoluene 193.2 g of 2,3-dichlorotoluene, 400 g of glacial acetic acid, 2.96 g of cobalt acetate tetrahydrate, 0.96 g of manganese acetate tetrahydrate, 1.65 g of sodium bromide and 1.97 g of sodium acetate are oxidized with air in the course of 2 hours at 155°–160° C. under 15–16 bar as in Example 1. The dichlorobenzoic acid which has crystallized is filtered off and dried. Colorless crystalline needles, melting point 166.0°–168.5° C.

The mother liquor is used as the reaction medium for the subsequent batches of 154.6 g of 2,3-dichlorotoluene as in Example 1. In the recyclings, 1.15 g of sodium acetate and 0.62 g of sodium bromide are added per batch and 0.82 g of sodium chloride is sluiced out. 0.014 mol of chloride per mole of 2,3-dichlorotoluene is formed.

The selectivity for 2,3-dichlorobenzoic acid is 96.9%.

Example 4

Oxidation of 4-chloro-4'-methylbenzophenone 279.0 g of 4-chloro-4'-methylbenzophenone, 1000 g of glacial acetic acid, 15.0 g of cobalt acetate tetrahydrate, 1.23 g of sodium bromide and 0.82 g of sodium acetate are oxidized with air in the course of one hour at 175° C. under 16 bar as in Example 1. The amount of chloride split off is 0.4 mol %. 0.40 g of sodium acetate and 0.33 g of HBr in the form of 1.0 g of a solution of 33% by weight HBr in glacial acetic acid are added per recycling. The selectivity for 4'-chloro-benzophenone-4-carboxylic acid is 97.4%. Melting point 253°–255° C.

We claim:

1. A process for the preparation of a halogen-substituted aromatic carboxylic acid by oxidation of the correspondingly halogen-substituted alkylaromatic with oxygen or an oxygen-containing gas, which comprises a procedure in which a) the reaction medium in which the oxidation reaction takes place contains an aromatic carboxylic acid substituted with at least one chlorine or bromine atom, acetic acid, a transition metal bromide catalyst, and an alkali metal salt of a weak acid, said salt being a sodium salt, a potassium salt, or a combination thereof;

b) when the reaction has ended, the reaction mixture is cooled and the resulting oxidized product is permitted to crystallize to form a crystallized product; the crystallized product is filtered off from the reaction mixture to obtain a mother liquor, and the mother liquor is combined with any wash liquors to obtain a combined liquor;

c) the combined liquor is dehydrated to a water content of $\leq 1.0\%$ by distillation, to obtain precipitation of alkali metal halide;

d) the alkali metal halide which has precipitated is filtered off from the combined liquor and e) the combined liquor is reused as the reaction medium.

2. The process as claimed in claim 1, wherein the alkali metal salt or salts is or are added before the reaction or during reuse of the combined liquor.

3. The process as claimed in claim 1, wherein the alkali metal salt is a salt of an aliphatic or aromatic carboxylic acid.

4. The process as claimed in claim 1, wherein the alkali metal salt is sodium acetate, potassium acetate, or a combination thereof, which is formed by addition of sodium or potassium carbonate or sodium or potassium hydroxide or a combination thereof to the acetic acid of the reaction medium.

5. The process as claimed in claim 1, wherein said halogen-substituted alkylaromatic is a chlorinated alkylaromatic, and said alkali metal salt is sodium acetate.

6. The process as claimed in claim 1, wherein said halogen-substituted alkylaromatic is a brominated alkylaromatic, and said alkali metal salt is potassium acetate.

7. The process as claimed in claim 1, wherein said transition metal bromide catalyst contains at least one of the metals cobalt, manganese, zirconium, or nickel.

8. The process as claimed in claim 1, wherein the reaction medium is cooled to 10° to 60° C. during said step (b).

9. The process as claimed in claim 1, wherein said halogenated alkylaromatic is a halogenated alkylphenyl or alkylnaphthyl compound, which compound is optionally further substituted.

10. The process as claimed in claim 1, wherein the aromatic carboxylic oxidation product is a compound of formula (I)

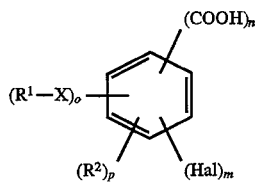

in which:

X is a single bond, oxygen, C=O, $SO_2$, $C(CF_3)_2$, $C(CH_3)_2$, PO-($C_1$-$C_6$)-alkyl, PO-phenyl, Si-($C_1$-$C_6$-alkyl)$_2$, Si-($C_1$-$C_6$-alkyl)-phenyl, Si-(phenyl)$_2$ or —$N_2$—, $R^1$ is substituted or unsubstituted phenyl or naphthyl, Hal is chlorine or bromine, $R^2$ is hydrogen, O-($C_1$-$C_6$)-alkyl, tert-alkyl, $SO_2$-($C_1$-$C_6$)-alkyl, $SO_2$-$NH_2$, $NO_2$, F, PO-[($C_1$-$C_6$)-alkyl]$_2$, PO(OH)-($C_1$-$C_6$)-alkyl or PO-(OH)$_2$, n and m are an integer between 1 and 4, where n+m≦5, and o and p are zero or 1, where n+m+o+p≦6.

11. The process as claimed in claim 1, wherein the aromatic carboxylic oxidation product is a chlorobenzoic acid, a dichlorobenzoic acid, a bromobenzoic acid, chlorinated or brominated benzophenonecarboxylic acid or chlorinated or brominated biphenylcarboxylic acid, and wherein said aromatic carboxylic oxidation product optionally includes a fluorine substituent.

12. The process as claimed in claim 1, wherein, in said step (c), said alkali metal halide includes sodium or potassium chloride, or a mixture thereof, and sodium or potassium bromide, or a mixture thereof, and wherein chloride ions are precipitated essentially selectively while the bromide ions are essentially retained.

13. The process as claimed in claim 12, wherein, in said step (c), said alkali metal halide includes NaCl and NaBr, and wherein NaCl is precipitated in preference to NaBr.

14. The process as claimed in claim 1, wherein: said halogenated alkylaromatic is a bromoaromatic compound; in said step (c), said alkali metal halide includes NaBr and KBr; and wherein KBr is precipitated in preference to NaBr.

15. The process as claimed in claim 1, wherein an alkali metal salt of the weak acid is a sodium or potassium salt of acetic acid, propionic acid, butyric acid or benzoic acid.

16. The process as claimed in claim 1, wherein the transition metal of said transition metal bromide catalyst comprises cobalt.

17. The process as claimed in claim 1, wherein the reaction medium is cooled to 20° to 30° C. during said step (b).

* * * * *